US012426771B2

(12) United States Patent
Iwasaki

(10) Patent No.: US 12,426,771 B2
(45) Date of Patent: Sep. 30, 2025

(54) ENDOSCOPE SYSTEM, IMAGE PROCESSING DEVICE, TOTAL PROCESSING TIME DETECTION METHOD, AND PROCESSING DEVICE

(71) Applicant: OLYMPUS CORPORATION, Tokyo (JP)

(72) Inventor: Tomoki Iwasaki, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 1141 days.

(21) Appl. No.: 17/350,657

(22) Filed: Jun. 17, 2021

(65) Prior Publication Data

US 2021/0307587 A1 Oct. 7, 2021

Related U.S. Application Data

(63) Continuation of application No. PCT/JP2019/008466, filed on Mar. 4, 2019.

(51) Int. Cl.
*A61B 1/00* (2006.01)
*A61B 1/045* (2006.01)
(Continued)

(52) U.S. Cl.
CPC .... *A61B 1/000095* (2022.02); *A61B 1/00018* (2013.01); *A61B 1/00045* (2013.01); *A61B 1/045* (2013.01); *A61B 1/0655* (2022.02)

(58) Field of Classification Search
CPC .......... A61B 1/000095; A61B 1/00018; A61B 1/00045; A61B 1/045; A61B 1/00004; A61B 1/00009; G16H 30/20; G16H 30/40
See application file for complete search history.

(56) References Cited

U.S. PATENT DOCUMENTS

| 8,970,686 B2 * | 3/2015 | Kobayashi | A61B 1/045 600/101 |
| 10,568,497 B2 * | 2/2020 | Nakagawa | A61B 1/05 |

(Continued)

FOREIGN PATENT DOCUMENTS

| CN | 105376480 A | 3/2016 |
| JP | 2004-121372 A | 4/2004 |

(Continued)

OTHER PUBLICATIONS

International Search Report dated Apr. 23, 2019 received in PCT/JP2019/008466.

(Continued)

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

An endoscope system includes: an endoscope configured to generate an imaging signal and output the generated imaging signal; an image processing device configured to perform image processing on the imaging signal input from the endoscope; a display configured to display an image of a subject based on the imaging signal subjected to the image processing by the image processing device; and a first processor configured to calculate a sum of a first processing time from when the endoscope generates the imaging signal to when the endoscope outputs the imaging signal, a second processing time from when the image processing device receives the imaging signal to when the image processing device outputs the imaging signal to the display, and a third processing time from when the display receives the imaging signal to when the display displays the image based on the imaging signal.

18 Claims, 8 Drawing Sheets

(51) Int. Cl.
*A61B 1/06* (2006.01)
*G16H 30/00* (2018.01)

(56) References Cited

U.S. PATENT DOCUMENTS

| | | | |
|---|---|---|---|
| 2007/0225551 A1 | 9/2007 | Kobayashi et al. | |
| 2012/0323073 A1* | 12/2012 | Azuma | A61B 1/00009 600/110 |
| 2014/0125839 A1* | 5/2014 | Shiohara | H04N 23/72 348/229.1 |
| 2016/0055662 A1 | 2/2016 | Tomidokoro | |
| 2019/0290108 A1 | 9/2019 | Nakamitsu et al. | |
| 2021/0177263 A1* | 6/2021 | Mizukura | G06T 7/0012 |

FOREIGN PATENT DOCUMENTS

| | | |
|---|---|---|
| JP | 2011-036488 A | 2/2011 |
| JP | 2015-036055 A | 2/2015 |
| JP | 2017-225648 A | 12/2017 |
| WO | 2017/126333 A1 | 7/2017 |
| WO | 2018/047730 A1 | 3/2018 |
| WO | 2018/116572 A1 | 6/2018 |

OTHER PUBLICATIONS

Japanese Office Action dated May 10, 2022 received in 2021-503298.
Chinese Office Action dated Jun. 21, 2024 received in 201980087161.X.
Chinese Office Action dated Jan. 9, 2024 received in 201980087161.X.

* cited by examiner

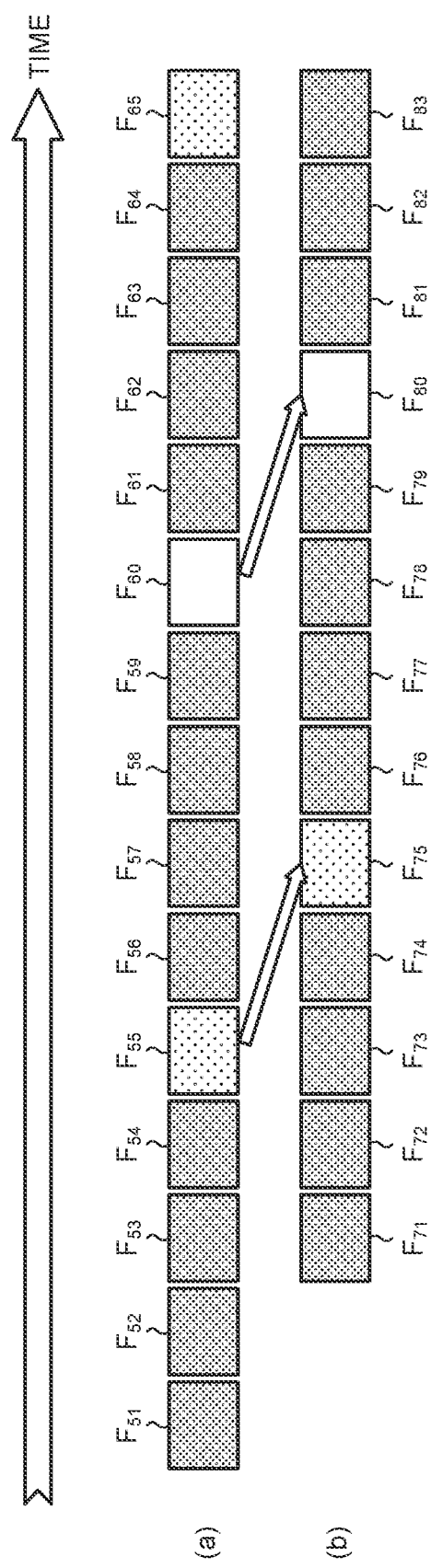

ENDOSCOPE SYSTEM, IMAGE PROCESSING DEVICE, TOTAL PROCESSING TIME DETECTION METHOD, AND PROCESSING DEVICE

CROSS-REFERENCE TO RELATED APPLICATION

This application is a continuation of International Application No. PCT/JP2019/008466, filed on Mar. 4, 2019, the entire contents of which are incorporated herein by reference.

BACKGROUND

1. Technical Field

The present disclosure relates to an endoscope system including an endoscope, an image processing device, a total processing time detection method, and a processing device.

2. Related Art

In the medical field, an endoscope system is used for observing the inside of a subject. In general, an endoscope inserts an elongated flexible insertion portion into a subject such as a patient, illuminates illumination light supplied by a light source device from a distal end of the insertion portion, and captures an in-vivo image by receiving reflected light of the illumination light by an imaging portion at the distal end of the insertion portion. The in-vivo image captured by the imaging portion of the endoscope is subjected to predetermined image processing in a processing device of the endoscope system, and then displayed on a display of the endoscope system, A user such as a doctor observes an organ of a subject on the basis of the in-vivo image displayed on the display.

Meanwhile, in the processing device, a processing time from acquisition of the in-vivo image to generation of image data for display varies depending on the type of image and the type of image processing. When the processing time is long, a time lag from when an image is captured by the endoscope to when the image is displayed on the display device is also long. When the time lag becomes long, a deviation may occur between an actual position of the endoscope in the subject and a position of the endoscope recognized by an operator viewing the display device, and the treatment to an appropriate position may not be performed.

As for the display time lag, technology for performing signal processing in consideration of a processing delay of an apparatus is known (for example, see JP 2011-036488 A). In JP 2011-036488 A, an image processing device and a processor are synchronized with each other, so that images displayed by display devices connected to the image processing device and the processor are synchronized with each other.

SUMMARY

In some embodiments, an endoscope system includes: an endoscope configured to capture an image of a subject, generate an imaging signal, and output the generated imaging signal; an image processing device configured to perform image processing on the imaging signal input from the endoscope; a display configured to display the image of the subject based on the imaging signal subjected to the image processing by the image processing device; and a first processor including hardware, the first processor being provided in any one of the endoscope, the image processing device, and the display, the first processor being configured to calculate a sum of a first processing time from when the endoscope generates the imaging signal to when the endoscope outputs the imaging signal, a second processing time from when the image processing device receives the imaging signal to when the image processing device outputs the imaging signal to the display, and a third processing time from when the display receives the imaging signal to when the display displays the image based on the imaging signal.

In some embodiments, provided is an image processing device that is connected to an endoscope and a display, the endoscope being configured to capture an image of a subject, generate an imaging signal, and output the generated imaging signal, the display being configured to display the image of the subject. The image processing device includes: a processor including hardware, the processor being configured to perform image processing on the imaging signal input from the endoscope, calculate a sum of a first processing time from when the endoscope generates the imaging signal to when the endoscope outputs the imaging signal, a second processing time from when the image processing device receives the imaging signal to when the image processing device outputs the imaging signal to the display, and a third processing time from when the display receives the imaging signal to when the display displays the image based on the imaging signal.

In some embodiments, a total processing time detection method includes: acquiring a first processing time from when an endoscope generates an imaging signal to when the endoscope outputs the imaging signal; acquiring a second processing time from when an image processing device receives the imaging signal to when the image processing device outputs the imaging signal to a display; acquiring a third processing time from when the display receives the imaging signal to when the display displays the image based on the imaging signal; and calculating a sum of the first processing time, the second processing time, and the third processing time.

In some embodiments, a processing device includes: an input portion configured to receive an imaging signal from an endoscope; an output portion configured to output a display image to a display; and a processor including hardware, the processor being configured to acquire a processing time from when the input portion receives the imaging signal to when the output portion outputs the display image, and perform notification processing when the processing time is equal to or more than a predetermined threshold.

In some embodiments, a processing device includes: an image processing circuit configured to execute first image processing and second image processing on an imaging signal, the second image processing partially different from the first image processing, a processing time of the second image processing being shorter than a processing time of the first image processing; and a control circuit configured to acquire a processing time from when an image sensor outputs an imaging signal to when a display displays an image, determine whether the processing time is equal to or more than a predetermined threshold, and perform switching from the first image processing to the second image processing when the processing time is equal to or more than the predetermined threshold.

In some embodiments, a processing device includes: a processor including hardware, the processor being configured to acquire a time from when the image sensor outputs an imaging signal to when a display displays an image generated based on the imaging signal, and perform notification when the time is equal to or more than a predetermined threshold.

In some embodiments, a processing device includes: a processor including hardware, the processor being configured to perform image processing on an imaging signal to generate an image, acquire a time from when an image sensor outputs the imaging signal to when a display displays the image, and switch the image processing from first image processing to second image processing when the time is equal to or more than a predetermined threshold, the second image processing being image processing in which a part of the first image processing is thinned out.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 9 is a diagram illustrating delay time acquisition processing performed by the endoscope system according to the fourth embodiment of the disclosure.

DETAILED DESCRIPTION

Figure 1:
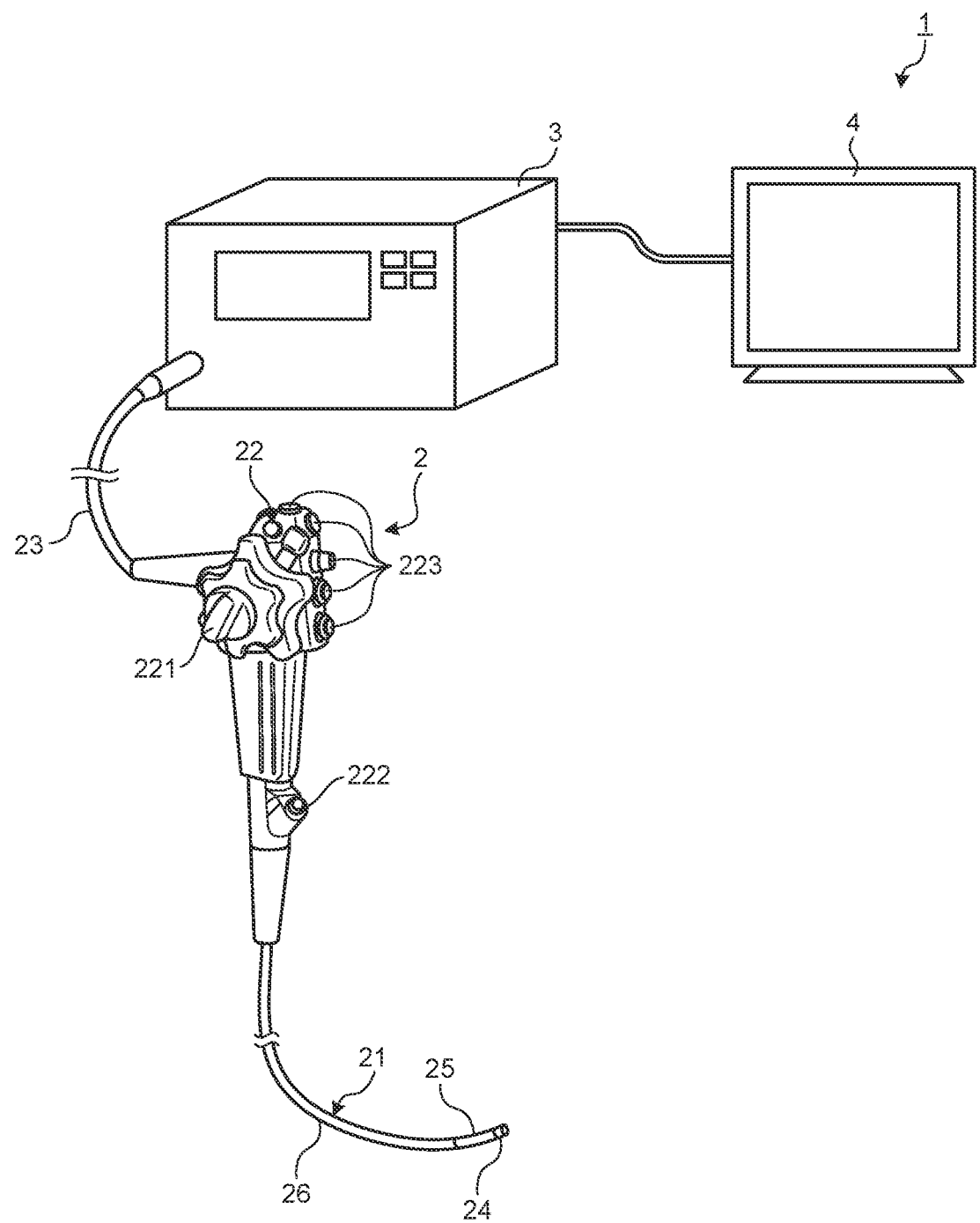
FIG. 1 is a diagram illustrating a schematic configuration of an endoscope system according to a first embodiment of the disclosure.

Hereinafter, embodiments of the disclosure will be described. In an embodiment, a medical endoscope system that images and displays a subject such as a patient will be described as an example of an endoscope system according to the disclosure. Further, the disclosure is not limited by the embodiment. Further, in the description of the drawings, the same components will be denoted by the same reference numerals.

First Embodiment

Figure 2:
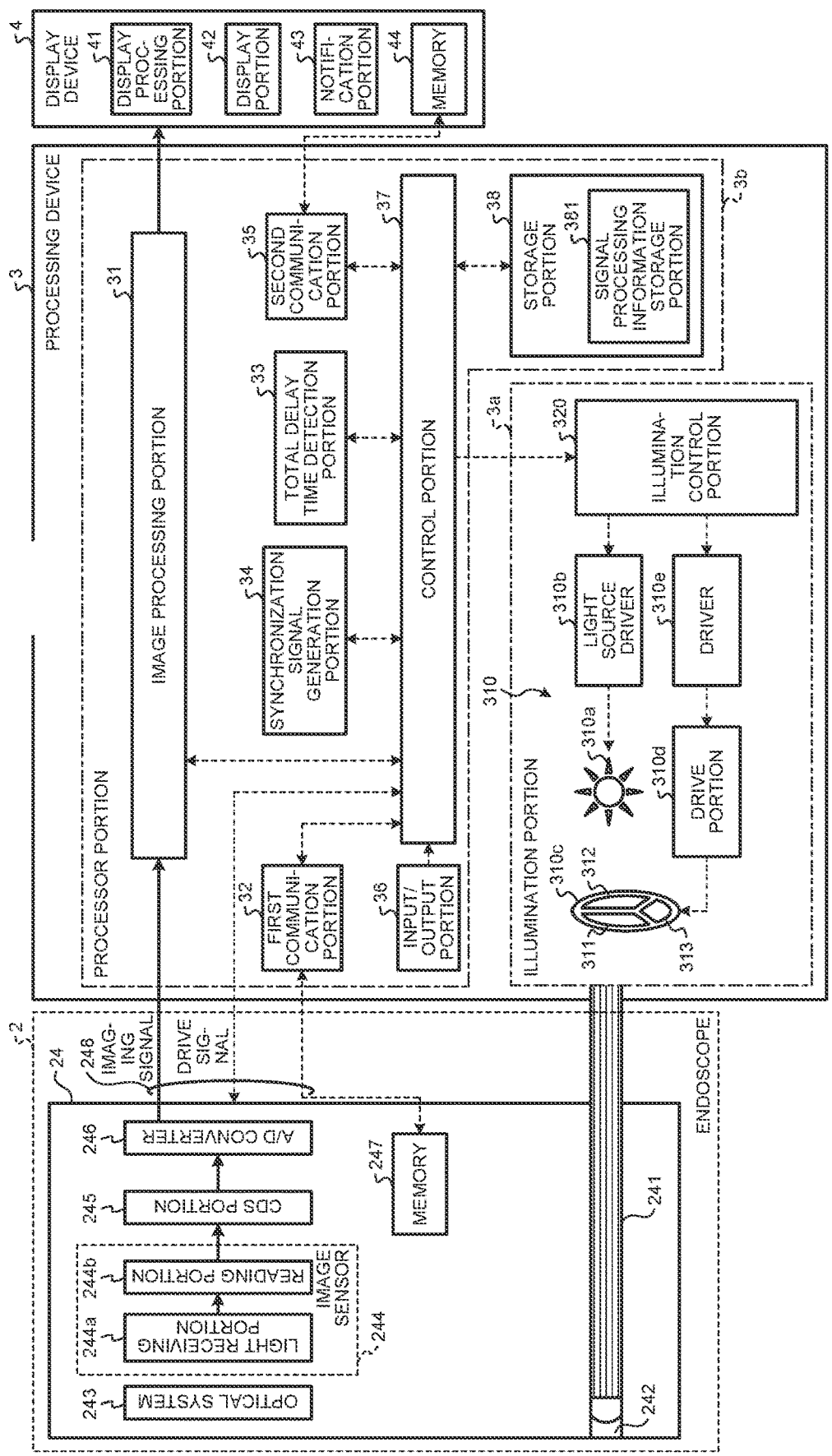
FIG. 2 is a block diagram illustrating a schematic configuration of the endoscope system according to the first embodiment of the disclosure.

FIG. 1 is a diagram illustrating a schematic configuration of an endoscope system according to a first embodiment of the disclosure. FIG. 2 is a block diagram illustrating a schematic configuration of the endoscope system according to the first embodiment.

An endoscope system 1 illustrated in FIGS. 1 and 2 includes an endoscope 2 that captures an image of a subject by inserting a distal end portion into the subject, a processing device 3 that has an illumination portion 3a generating illumination light emitted from the distal end of the endoscope 2, performs predetermined signal processing on an imaging signal captured by the endoscope 2, and generally controls the entire operation of the endoscope system 1, and a display device 4 that displays an in-vivo image generated by the signal processing of the processing device 3.

The endoscope 2 includes an insertion portion 21 that has a flexible elongated shape, an operating portion 22 that is connected to the side of a proximal end of the insertion portion 21 and receives inputs of various operation signals, and a universal cord 23 that extends in a direction different from a direction where the insertion portion 21 extends from the operating portion 22 and incorporates various cables connected to the processing device 3 (including the illumination portion 3a).

The insertion portion 21 includes a distal end portion 24, a bending portion 25, and an elongated tube portion 26. The distal end portion 24 incorporates an image sensor 244 in which pixels generating a signal by receiving light and performing photoelectric conversion are two-dimensionally arranged. The bending portion 25 is bendable and includes a plurality of bending pieces. The elongated flexible tube portion 26 is connected to the side of a proximal end of the bending portion 25 and has flexibility. The insertion portion 21 is inserted into a body cavity of the subject and captures an image of the subject such as a living tissue at a position where external light does not reach by the image sensor 244.

The distal end portion 24 has a light guide 241 that is configured using a glass fiber or the like and forms a light guide path of light emitted by the illumination portion 3a, an illumination lens 242 that is provided at a distal end of the light guide 241, a condensing optical system 243, the image sensor 244 that is provided at an image forming position of the optical system 243, receives light condensed by the optical system 243, and photoelectrically converts the light into an electric signal, a correlated double sampling (CDS) portion 245 that reduces a noise component included in an analog imaging signal using a CDS method, an A/D converter 246 that converts the analog imaging signal output through the CDS portion 245 into a digital signal, and a memory 247.

The optical system 243 is configured using one or more lenses, and has an optical zoom function for changing an angle of view and a focus function for changing a focal point.

The image sensor 244 photoelectrically converts the light from the optical system 243 to generate an electric signal (image signal). Specifically, the image sensor 244 has a light receiving portion 244a in which a plurality of pixels, each of which has a photodiode accumulating a charge according to a light amount, a capacitor converting the charge transferred from the photodiode into a voltage level, and the like, are arranged in a matrix, and each pixel photoelectrically converts the light from the optical system 243 to generate an electric signal, and a reading portion 244b that sequentially reads the electric signal generated by a pixel arbitrarily set as a reading target among the plurality of pixels of the light receiving portion 244a and outputs the electric signal as an imaging signal. An imaging signal including image data constituting information of a display image is output from the image sensor 244. The image sensor 244 is realized by using, for example, a charge coupled device (CCD) image sensor or a complementary metal oxide semiconductor (CMOS) image sensor.

The memory 247 stores an execution program and a control program to execute various operations by the image sensor 244, identification information of the endoscope 2, and a delay time required for signal processing in the endoscope 2. The identification information includes identification information (ID) of the endoscope 2, a model year, specification information, a transmission method, and the like. Further, the memory 247 may temporarily store image data or the like generated by the image sensor 244. The delay time corresponds to a delay time of data transmission caused by the signal processing, and is set by the number of frames here. Specifically, the delay time is a value obtained by converting a time from the start of reading by the reading portion 244b to the completion of the conversion processing of the A/D converter 246 into the number of frames. The memory 247 includes a random access memory (RAM), a read only memory (ROM), a flash memory, and the like.

The operating portion 22 includes a bending knob 221 that bends the bending portion 25 in a vertical direction and a horizontal direction, a treatment tool insertion portion 222 that inserts a treatment tool such as biopsy forceps, an electric scalpel, and an inspection probe into the body cavity of the subject, and a plurality of switches 223 that are operation input/output portions inputting operation instruction signals of peripheral devices such as an air supply unit, a water supply unit, and screen display control, in addition to the processing device 3, The treatment tool inserted from the treatment tool insertion portion 222 comes out from an aperture portion (not illustrated) via a treatment tool channel (not illustrated) of the distal end portion 24.

The universal cord 23 incorporates at least the light guide 241 and an assembly cable 248 including a plurality of signal lines. The assembly cable 248 includes a signal line for transmitting an imaging signal, a signal line for transmitting a drive signal for driving the image sensor 244, and a signal line for transmitting and receiving information including identification information regarding the endoscope 2 (image sensor 244) and the like. Note that, in the present embodiment, transmitting the electric signal using a signal line is described, but an optical signal may be transmitted, or a signal may be transmitted between the endoscope 2 and the processing device 3 by wireless communication.

Next, a configuration of the processing device 3 will be described. The processing device 3 includes the illumination portion 3a and a processor portion 3b. The processor portion 3b includes an image processing portion 31, a first communication portion 32, a total delay time detection portion 33, a synchronization signal generation portion 34, a second communication portion 35, an input/output portion 36, a control portion 37, and a storage portion 38. The processor portion 3b corresponds to an image processing device.

First, a configuration of the illumination portion 3a will be described. The illumination portion 3a includes a light source portion 310 and an illumination control portion 320.

The light source portion 310 is configured using a light source that emits illumination light, a plurality of lenses, a filter that passes light in a predetermined wavelength band, and the like, and emits illumination light of the light in the predetermined wavelength band. The light source portion 310 has a light source 310a, a light source driver 310b, a rotating filter 310c, a drive portion 310d, and a driver 310e.

The light source portion 310 is configured using a white LED, one or more lenses, and the like, and emits white light to the rotating filter 310c under the control of the light source driver 310b. The white light generated by the light source 310a is emitted from the distal end of the distal end portion 24 to the subject via the rotating filter 310c and the light guide 241.

The light source driver 310b supplies a current to the light source 310a under the control of the illumination control portion 320 to cause the light source 310a to emit white light.

The rotating filter 310c is disposed on an optical path of the white light emitted from the light source 310a, and rotates to transmit only light in a predetermined wavelength band among the white light emitted from the light source 310a. Specifically, the rotating filter 310c has a red filter 311, a green filter 312, and a blue filter 313 that transmit light having wavelength bands of red light (R), green light (G), and blue light (B), respectively. The rotating filter 310c rotates to sequentially transmit light in red, green, and blue wavelength bands (for example, red: 600 nm to 700 nm, green: 500 nm to 600 nm, and blue: 400 nm to 500 nm). As a result, any one of red light (R illumination), green light (G illumination), and blue light (B illumination) can be sequentially emitted to the endoscope 2 using the white light (W illumination) emitted from the light source 310a (frame sequential method).

The drive portion 310d includes a stepping motor, a DC motor, or the like, and rotates the rotating filter 310c.

The driver 310e supplies a predetermined current to the drive portion 310d under the control of the illumination control portion 320.

The illumination control portion 320 controls an amount of current to be supplied to the light source 310a, on the basis of the control signal from the control portion 37. Further, the illumination control portion 320 drives the drive portion 310d via the light source driver 310b under the control of the control portion 37 to rotate the rotating filter 310c.

Note that the light source 310a may include a red LED, a green LED, and a blue LED, and the light source driver 310b may supply a current to each LED to sequentially emit red light, green light, or blue light. In addition, light may be simultaneously emitted from a white LED, a red LED, a green LED, and a blue LED, or an image may be acquired by irradiating the subject with white light using a laser, a discharge lamp such as a xenon lamp, or the like.

The image processing portion 31 receives an imaging signal of the illumination light of each color imaged by the image sensor 244 from the endoscope 2. The image processing portion 31 performs predetermined image processing on the imaging signal received from the endoscope 2, generates an imaging signal for display, and outputs the imaging signal to the display device 4. The image processing portion 31 includes one or a combination of a general-purpose processor such as a central processing portion (CPU) and a dedicated processor such as various arithmetic circuits executing specific functions such as an application specific integrated circuit (ASIC) and a field programmable gate array (FPGA) to be a programmable logic device capable of rewriting processing contents.

Figure 3:
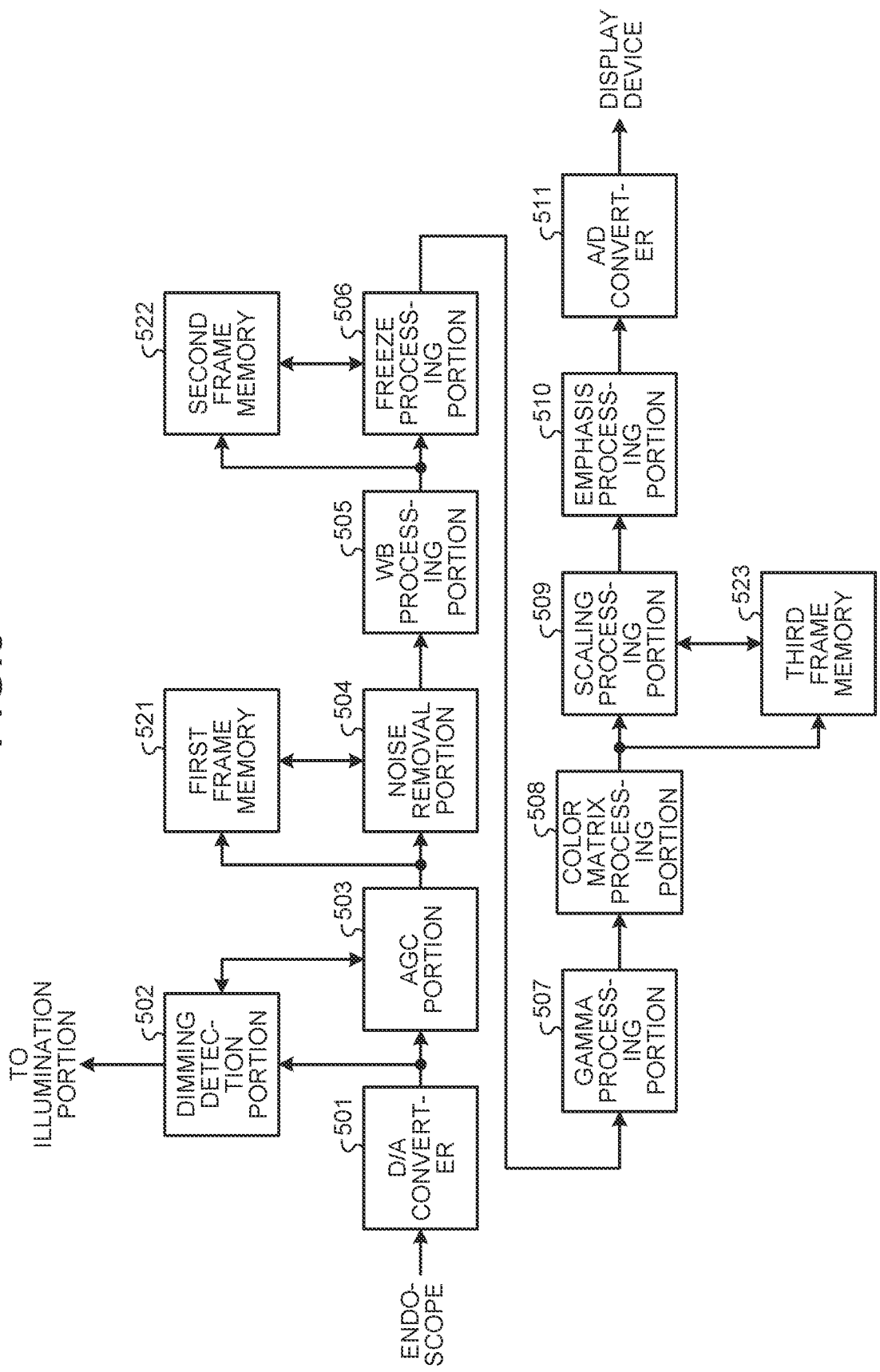
FIG. 3 is a diagram illustrating a configuration of an image processing portion included in the endoscope system according to the first embodiment of the disclosure.

FIG. 3 is a diagram illustrating a configuration of the image processing portion included in the endoscope system according to the first embodiment of the disclosure. The image processing portion 31 has a D/A converter 501, a dimming detection portion 502, an automatic gain control (AGC) portion 503, a noise removal portion 504, a white balance (WB) processing portion 505, a freeze processing portion 506, a gamma processing portion 507, a color matrix processing portion 508, a scaling processing portion 509, an emphasis processing portion 510, an A/D converter 511, a first frame memory 521, a second frame memory 522, and a third frame memory 523.

The D/A converter 501 converts a digital imaging signal input from the endoscope 2 into an analog signal. Hereinafter, the image processing portion 31 performs various types of processing on data (image data) related to image display among the data included in the imaging signal.

The dimming detection portion 502 detects a brightness level corresponding to each image, on the basis of RGB image information included in the image data input from the D/A converter 501. The dimming detection portion 502 sets light emission conditions such as an amount of light generated by the illumination portion 3a and light emission timing, on the basis of the detected brightness level.

The AGC portion 503 performs processing of adjusting an amplification factor (gain) of a signal value on the image data to maintain a constant output level. The AGC portion 503 performs gain adjustment according to the light emission conditions set by the dimming detection portion 502.

The noise removal portion 504 performs noise reduction processing on the image data input from the AGC portion 503. The noise removal portion 504 acquires image data of a previous frame with reference to, for example, the first frame memory 521, and removes noise using the acquired image data and image data to be subjected to noise removal processing. A known method can be used for the noise reduction processing.

The WB processing portion 505 performs processing of correcting white balance on the image data after the noise removal processing. A known method can be used for the white balance correction processing.

When the input of the freeze instruction signal is received by pressing the switch 223, the freeze processing portion 506 refers to the second frame memory 522 and selects image data to be frozen and displayed on the display device 4. The freeze processing portion 506 outputs the selected image data to the gamma processing portion 507. The freeze processing portion 506 selects image data with small blurring from the image data stored in the second frame memory 522, for example.

On the other hand, when the input of the freeze instruction signal is not received, the freeze processing portion 506 outputs predetermined image data in the second frame memory 522, for example, image data with the latest acquisition (imaging) time to the gamma processing portion 507. Here, when the latest image data is acquired, the freeze processing portion 506 may acquire the image data from the WB processing portion 505.

After selecting the image data to be frozen, the freeze processing portion 506 performs only processing of outputting the image data input from the WB processing portion 505 to the second frame memory 522 during a still image display period by freeze processing, After the freeze processing is canceled, the freeze processing portion 506 selects the latest image data from the second frame memory 522, including the image data newly input from the WB processing portion 505. For this reason, in the image displayed on the display device 4 after the freeze processing, an image in which the latest image data in the still image display period by the freeze processing is omitted and which is spaced apart in time series from that before the freeze processing, Due to the omission in the image data of a predetermined number of frames, a change in the subject image may be larger in the images displayed before and after the freeze processing as compared with a case where images adjacent in time series are displayed as moving images.

The gamma processing portion 507 performs gamma correction processing on the image data input from the freeze processing portion 506. The gamma processing portion 507 performs, on the image data, gradation correction for increasing the brightness of a dark portion having a small luminance by using a preset y value, A known method can be used for the gamma correction processing.

The color matrix processing portion 508 performs color correction for improving color reproducibility on the image data input from the gamma processing portion 507, The color matrix processing portion 508 uniformly manages different colors among devices for the image data. The color matrix processing portion 508 uniformly manages colors between the endoscope 2, the processing device 3, and the display device 4, for example. The color matrix processing portion 508 is configured using a color management system (CMS). A known method can be used for the color matrix processing.

The scaling processing portion 509 performs processing of changing the size of the image data, according to a preset enlargement ratio or a preset reduction ratio, or an enlargement ratio or a reduction ratio input via the input/output portion 36. Note that the processing of the scaling processing portion 509 may not be enlarged or reduced by setting. The propriety of the zoom processing may be switched according to, for example, information received by the input/output portion 36.

The emphasis processing portion 510 performs contour emphasis processing on the image data after the scaling processing. By the emphasis processing of the emphasis processing portion 510, image data in which a contour is more clearly expressed is generated. A known method can be used for the contour emphasis processing.

The A/D converter 511 converts the analog image data output through the emphasis processing portion 510 into a digital signal. The A/D converter 511 outputs the image data after the digital conversion to the display device 4 as an imaging signal for image display.

The first frame memory 521, the second frame memory 522, and the third frame memory 523 store the image data generated by the connected portions for the set frames. In the first embodiment, each frame memory stores image data of several frames. When new image data is input, each frame memory overwrites the oldest image data with the new image data among the currently stored image data, thereby sequentially updating and storing image data for several frames in order from the latest acquisition time. The first frame memory 521, the second frame memory 522, and the third frame memory 523 are configured using a random access memory (RAM), for example, a video RAM (VRAM).

When the endoscope 2 is connected, the first communication portion 32 acquires the processing time stored in the memory 247 of the endoscope 2. The first communication portion 32 is configured using a general-purpose processor such as a CPU or a dedicated processor such as various arithmetic circuits executing specific functions such as an ASIC.

The total delay time detection portion 33 detects a delay time required for signal processing from generation of an imaging signal for one frame to display of image data on the display device 4 in the endoscope 2, the processing device 3, and the display device 4. Specifically, the total delay time detection portion 33 calculates the sum of the delay time of the endoscope 2, the delay time of the processing device 3, and the delay time of the display device 4. A value calculated by the total delay time detection portion 33 in the first embodiment is a value obtained by converting the total delay time into the number of frames. The total delay time detection portion 33 is configured using a general-purpose processor such as a CPU or a dedicated processor such as various arithmetic circuits executing specific functions such as an ASIC.

The synchronization signal generation portion 34 generates a clock signal (synchronization signal) serving as a reference of the operation of the processing device 3, and outputs the generated synchronization signal to the illumination portion 3a, the image processing portion 31, the control portion 37, and the endoscope 2. Here, the synchronization signal generated by the synchronization signal generation portion 34 includes a horizontal synchronization signal and a vertical synchronization signal.

Therefore, the illumination portion 3a, the image processing portion 31, the control portion 37, and the endoscope 2 operate in synchronization with each other according to the generated synchronization signal.

The synchronization signal generation portion 34 is configured using a general-purpose processor such as a CPU or a dedicated processor such as various arithmetic circuits executing specific functions such as an ASIC.

When the display device 4 is connected, the second communication portion 35 acquires a processing time required for the signal processing in the display device 4, which is stored in a memory 44 of the display device 4. The second communication portion 35 is configured using a general-purpose processor such as a CPU or a dedicated processor such as various arithmetic circuits executing specific functions such as an ASIC.

The input/output portion 36 is realized by using a keyboard, a mouse, a switch, and a touch panel, and receives inputs of various signals such as an operation instruction signal that instructs an operation of the endoscope system 1. Further, the input/output portion 36 is realized by using at least one of a speaker and a light source, and outputs sound or light. Note that the input/output portion 36 may include a switch provided in the operating portion 22 or a portable terminal such as an external tablet computer.

The control portion 37 performs drive control of each component including the image sensor 244 and the illumination portion 3a, input/output control of information with respect to each component, and the like. The control portion 37 refers to control information data (for example, reading timing or the like) for imaging control stored in the storage portion 38, and transmits the control information data as a drive signal to the image sensor 244 via a predetermined signal line included in the assembly cable 248. The control portion 37 is configured using a general-purpose processor such as a CPU or a dedicated processor such as various arithmetic circuits executing specific functions such as an ASIC.

The storage portion 38 stores various programs for operating the endoscope system 1, data including various parameters and the like necessary for the operation of the endoscope system 1, and a delay time required for signal processing in the processing device 3. Further, the storage portion 38 stores identification information of the processing device 3. Here, the identification information includes identification information (ID), a model year, specification information, and the like of the processing device 3. The processing time corresponds to a delay time of data transmission caused by signal processing in the processing device 3, and is a value obtained by converting a time from when image data is input from the endoscope 2 to when the image data is output to the display device 4 into the number of frames. Further, the storage portion 38 has a signal processing information storage portion 381 that stores signal processing conditions for controlling signal processing in the entire system including the endoscope 2 and the display device 4. The signal processing information storage portion 381 stores, for example, one or more thresholds set for the total delay time detected by the total delay time detection portion 33.

Further, the storage portion 38 stores various programs including an image acquisition processing program for executing an image acquisition processing method of the processing device 3. The various programs can be recorded on a computer-readable recording medium such as a hard disk, a flash memory, a CD-ROM, a DVD-ROM, or a flexible disk and widely distributed. Note that the above-described various programs can also be acquired by being downloaded via a communication network. Here, the communication network is realized by, for example, an existing public line network, a local area network (LAN), a wide area network (WAN), or the like, and may be a wired or wireless network.

The storage portion 38 having the above configuration is realized by using a read only memory (ROM) in which various programs and the like are previously installed and a RAM, a hard disk, and the like that store calculation parameters, data, and the like of each processing.

The display device 4 displays a display image corresponding to the image data received from the processing device 3 (image processing portion 31) via a video cable. The display device 4 includes a display processing portion 41, a display portion 42, and the memory 44.

The display processing portion 41 performs predetermined processing, for example, synchronization processing, format conversion, or the like, on the image data received from the processing device 3, and outputs the image data to the display portion 42. The synchronization processing is processing of synchronizing each of R image data based on image data generated by the image sensor 244 when the light source portion 310 emits the R illumination light, G image data based on image data generated by the image sensor 244 when the light source portion 310 emits the G illumination light, and B image data based on image data generated by the image sensor 244 when the light Source portion 310 emits the B illumination light.

The display portion 42 is configured using a monitor such as liquid crystal or organic electro luminescence (EL).

A notification portion 43 is realized by using at least one of a speaker and a light source, and outputs sound or light. The notification portion 43 emits sound and light according to the degree of display delay.

In the memory 44, a processing time for storing an execution program and a control program to execute various operations by the display device 4, or a processing time required for signal processing in the display device 4 corresponds to a delay time of data transmission caused by the signal processing, and is a value obtained by converting a time from when image data is input from the processing device 3 to when the image data is displayed on the display portion 42 into the number of frames. The memory 44 includes a RAM, a ROM, a flash memory, and the like.

Figure 4:
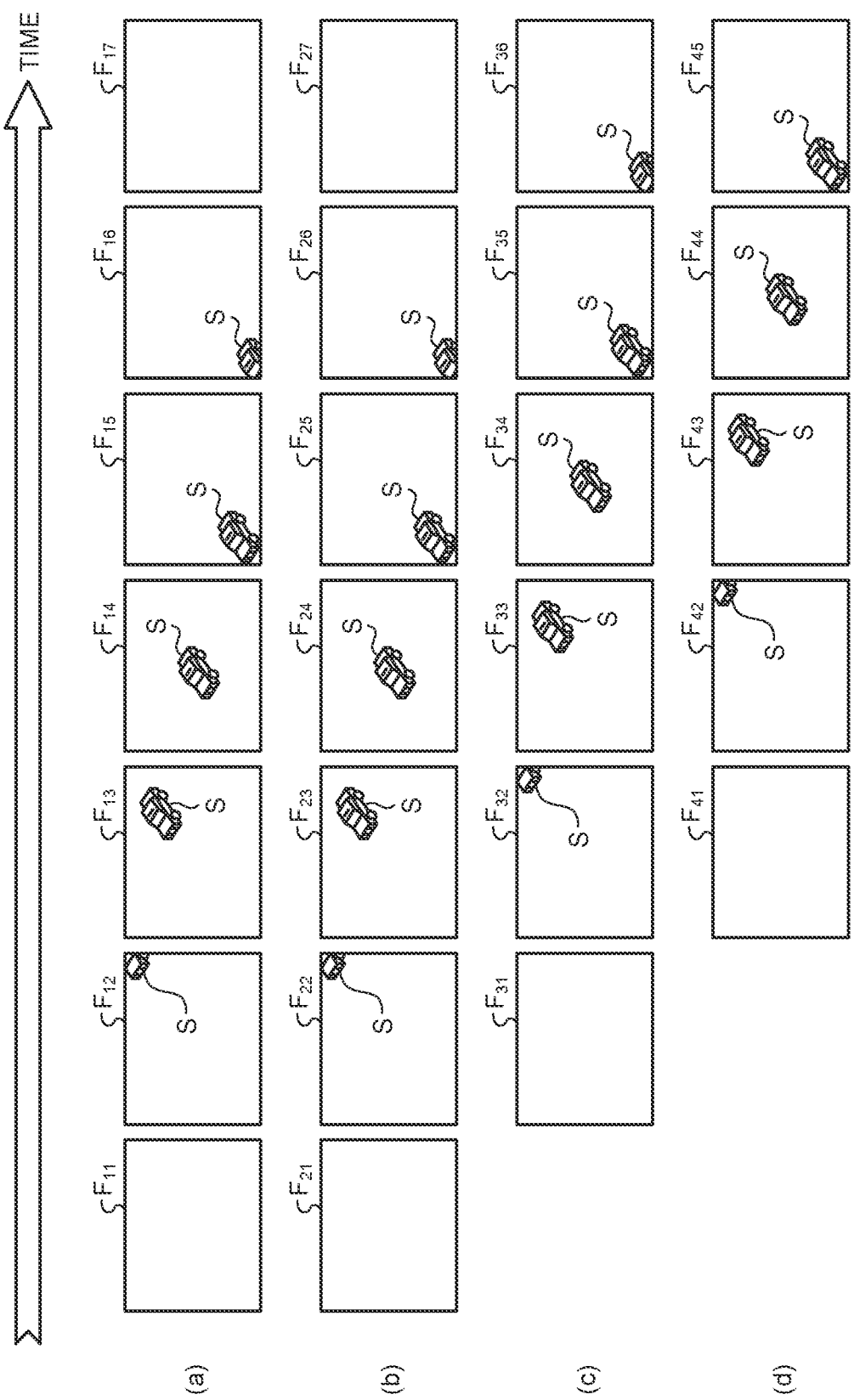
FIG. 4 is a diagram illustrating an image displayed by image processing performed by the endoscope system according to the first embodiment of the disclosure.

Here, an image captured by the endoscope 2 and an image displayed on the display device 4 in a case where signal processing is delayed in the endoscope system 1 will be described with reference to FIG. 4. FIG. 4 is a diagram illustrating an image displayed by image processing performed by the endoscope system according to the first embodiment of the disclosure, and is a timing chart illustrating imaging timing and display timing. In FIG. 4, a horizontal axis represents the lapse of time. (a) of FIG. 4 illustrates an image captured by the image sensor 244 of the endoscope 2. (b) of FIG. 4 illustrates an image displayed on display device 4 without delay. (c) of FIG. 4 illustrates an image displayed on the display device 4 when the display time is delayed by one frame. (d) of FIG. 4 illustrates an image displayed on the display device 4 when the display time is delayed by two frames.

In the endoscope 2, image data for one frame is sequentially captured (see (a) of FIG. 4). Specifically, images are sequentially captured in the order of images $F_{11}$, $F_{12}$, $F_{13}$, ..., $F_{16}$, $F_{17}$, .... A subject S is captured in the images $F_{12}$, $F_{13}$, ..., and $F_{16}$.

In a case where the image data captured by the endoscope 2 is displayed on the display device 4 through the above-described processing, if no delay occurs in each processing, the image data of each frame is sequentially displayed (see (b) of FIG. 4). Specifically, images $F_{21}$, $F_{22}$, $F_{23}$, ..., $F_{26}$, and $F_{27}$ corresponding to the images $F_{11}$, $F_{12}$, $F_{13}$, ..., $F_{16}$, and $F_{17}$ are sequentially displayed. Each image (images $F_{21}$, $F_{22}$, $F_{23}$, ..., $F_{26}$, $F_{27}$, ...) is displayed on the display device 4 at the same timing as the imaging timing in the endoscope 2.

On the other hand, when a delay occurs during a period until an image is captured by the endoscope 2 and is then displayed on the display device 4 through the above-described processing, the image data of each frame is sequentially displayed with a delay corresponding to the delay (see (b) and (c) of FIG. 4). For example, when a delay of one frame occurs, images $F_{31}$, $F_{32}$, $F_{33}$, ..., and $F_{36}$ corresponding to the images $F_{11}$, $F_{12}$, $F_{13}$, ..., and $F_{16}$ are displayed on the display device 4 after being delayed by one frame with respect to the imaging timing in the endoscope 2 (see (b) of FIG. 4). Further, when a delay of two frames occurs, images $F_{41}$, $F_{42}$, $F_{43}$, $F_{44}$, and $F_{45}$ corresponding to the images $F_{11}$, $F_{12}$, $F_{13}$, $F_{14}$, and $F_{15}$ are displayed on the display device 4 after being delayed by two frames with respect to the imaging timing in the endoscope 2 (see (c) of FIG. 4).

When the display is delayed in units of frames, for example, when the display is delayed by two frames, while the distal end portion 24 of the endoscope 2 is at a position where the image $F_{13}$ is captured, the image $F_{41}$ according to the image $F_{11}$ is displayed on the display portion 42 of the display device 4. In this case, a deviation occurs between the actual position of the endoscope 2 and the position of the endoscope 2 which is recognized by the operator and is identified from the image displayed on the display portion 42. If the number of delayed frames increases, the deviation also increases accordingly.

In the first embodiment, when the above-described display delay occurs, the notification portion 43 is caused to execute notification processing according to the degree of delay.

Figure 5:
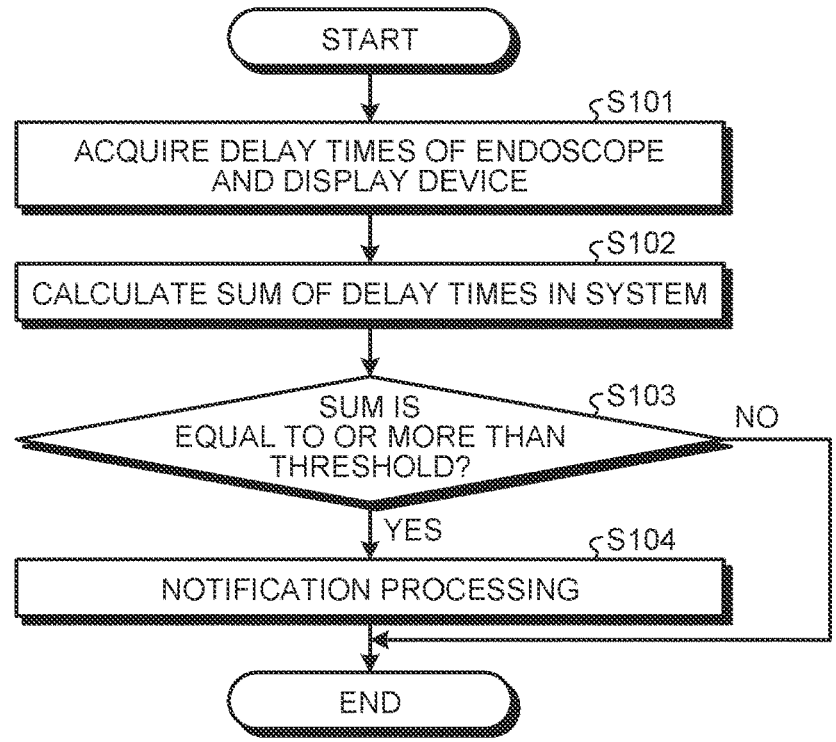
FIG. 5 is a flowchart illustrating delay detection processing performed by the endoscope system according to the first embodiment of the disclosure.

Next, delay detection processing performed by the endoscope system 1 will be described. FIG. 5 is a flowchart illustrating the delay detection processing performed by the endoscope system according to the first embodiment of the disclosure.

When the endoscope 2 and the display device 4 are connected after power is supplied, the processing device 3 acquires processing information (delay time) of each device from the memories 247 and 44 (step S101).

In step S102 following step S101, the total delay time detection portion 33 refers to the storage portion 38 to acquire the processing time (delay time) in the processing device 3, and calculates the sum of the delay times of the respective devices.

In step S103 following step S102, the control portion 37 compares the sum of the delay times of the respective devices with a threshold, and determines whether or not a delay to be notified can occur, Here, the threshold is preset and stored in the storage portion 38, and is a value determined by the number of frames. As the threshold, for example, three or more frames are set. Note that the threshold may be set (changed) in accordance with the information received by the input/output portion 36 and associated with the threshold set by the user such as the operator.

Here, when the control portion 37 determines that the sum of the delay times of the respective devices is equal to or more than the threshold, that is, a delay to be notified can occur on the basis of the sum (step S103: Yes), the control portion 37 proceeds to step S104. On the other hand, when the control portion 37 determines that the sum of the delay times of the respective devices is less than the threshold, that is, that no delay to be notified occurs on the basis of the sum (step S103: No), the control portion 37 ends the delay detection processing.

In step S104, the control portion 37 causes the notification portion 43 of the display device 4 to notify that a delay occurs in the displayed image. The notification portion 43 outputs sound or light to notify the operator that a deviation occurs between the actual position of the endoscope 2 and the position of the endoscope 2 recognized by the operator.

At this time, the intensity of the notification may be changed stepwise. For example, a plurality of thresholds for notification may be set, and the loudness of sound and the intensity of light may be changed when the total delay time (the number of frames) increases.

In addition to the notification portion 43, the input/output portion 36 may execute the notification processing.

In the first embodiment described above, the delay time generated by the image generation processing in each of the endoscope 2, the processing device 3, and the display device 4 is detected, and the notification portion 43 notifies the delay time according to the detection result. The operator can determine that the position of the distal end portion 24 of the endoscope 2 recognized by the operator from the display image is deviated from the actual position by the notification processing of the notification portion 43. According to the first embodiment, it is possible to suppress the deviation between the actual position of the endoscope 2 and the position of the endoscope 2 recognized by the operator observing the display image.

Note that, in the first embodiment, the example in which the notification portion 43 performs the notification processing according to the degree of delay has been described, but information indicating that a deviation occurs between the actual position of the endoscope 2 and the position of the endoscope 2 recognized by the operator may be displayed on the display portion 42.

Second Embodiment

Figure 6:
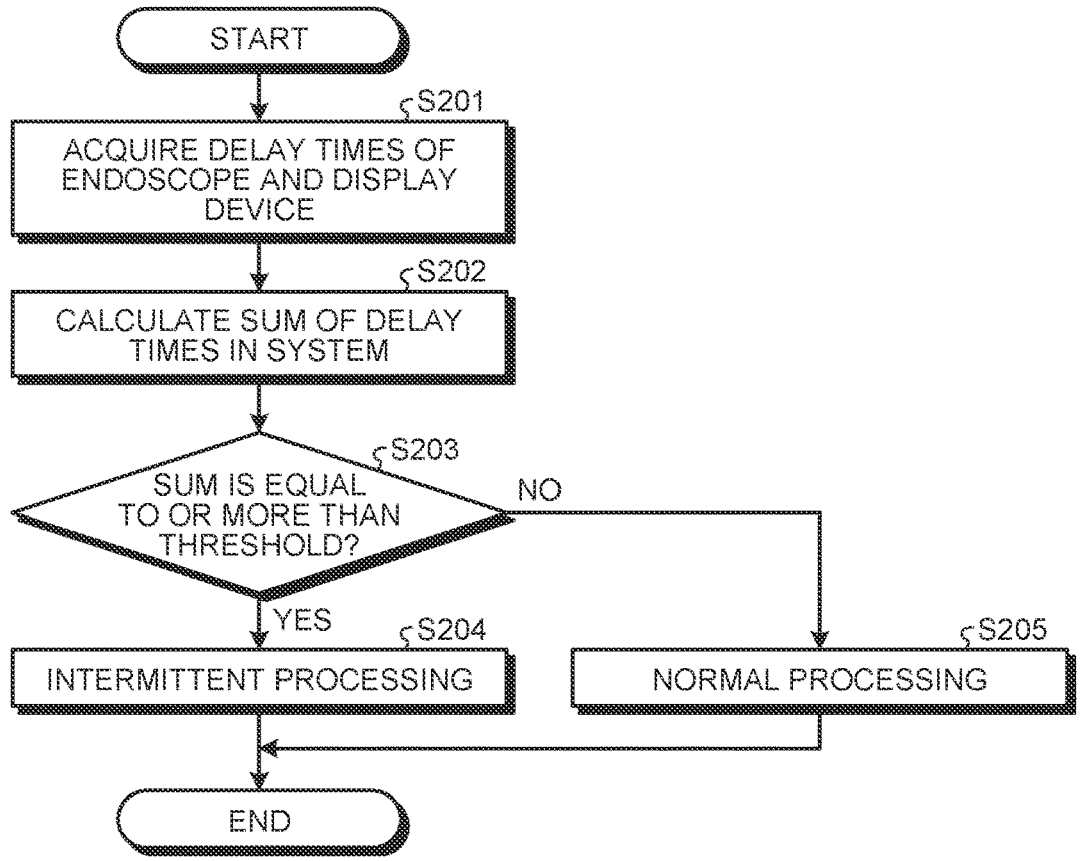
FIG. 6 is a flowchart illustrating delay detection processing performed by an endoscope system according to a second embodiment of the disclosure.

Next, a second embodiment of the disclosure will be described with reference to FIG. 6. FIG. 6 is a flowchart illustrating delay detection processing performed by an endoscope system according to the second embodiment of the disclosure. Note that, since a configuration of the endoscope system according to the second embodiment is the same as that of the above-described endoscope system, the description thereof will be omitted. Hereinafter, processing different from that of the first embodiment will be described.

When an endoscope 2 and a display device 4 are connected after power is supplied, a processing device 3 acquires processing information (delay time) of each device from memories 247 and 44 (step S201).

In step S202 following step S201, a total delay time detection portion 33 refers to a storage portion 38 to acquire the processing time (delay time) in the processing device 3, and calculates the sum of the delay times of the respective devices.

In step S203 following step S202, a control portion 37 compares the sum of the delay times of the respective devices with a threshold, and determines whether or not a delay to be notified can occur. Here, the threshold is the same as that in the first embodiment.

Here, when the control portion 37 determines that the sum of the delay times of the respective devices is equal to or more than the threshold, that is, a delay to be notified can occur on the basis of the sum (step S203: Yes), the control portion 37 proceeds to step S204. On the other hand, when the control portion 37 determines that the sum of the delay times of the respective devices is less than the threshold, that is, no delay to be notified occurs on the basis of the sum (step S203: No), the control portion 37 proceeds to step S205.

In step S204, the control portion 37 causes an image processing portion 31 to perform intermittent processing. In the intermittent processing, a part of the processing is thinned out according to the total delay time (the number of frames). Examples of processing of a thinning-out target include freeze processing, emphasis processing, and the like. When the total delay time is longer (the number of frames is larger), the number of thinning-out processing also increases. At this time, the thinning-out priority order of each processing is preset and stored in the storage portion 38. The control portion 37 determines thinning-out processing with reference to the total delay time and the priority order.

Note that, when processing of generating an all-in-focus image by combining images at different focal points, processing of generating a three-dimensional image, processing corresponding to 4K resolution, color shift correction processing of a moving image, and the like are performed, these processing are processing to be thinned out.

In addition, the delay time may be reduced by imposing restrictions on the monitor output format, or when Display Port, HDMI, or DVI is used, a change to SDI or the like may be prompted. By changing to the SDI, the delay time can be reduced as compared with Display Port, HDMI, and DVI.

On the other hand, in step S205, the control portion 37 causes the image processing portion 31 to perform normal processing. In the normal processing, each portion (see FIG. 3) of the above-described image processing portion 31 is caused to execute processing.

In the second embodiment described above, the delay time generated by the image generation processing in each of the endoscope 2, the processing device 3, and the display device 4 is detected, and contents of the image processing are changed according to the detection result. According to the second embodiment, the delay is eliminated by thinning out a part of the image processing, and as a result, it is possible to suppress a deviation between an actual position of the endoscope 2 and a position of the endoscope 2 recognized by an operator observing a display image.

Third Embodiment

Figure 7:
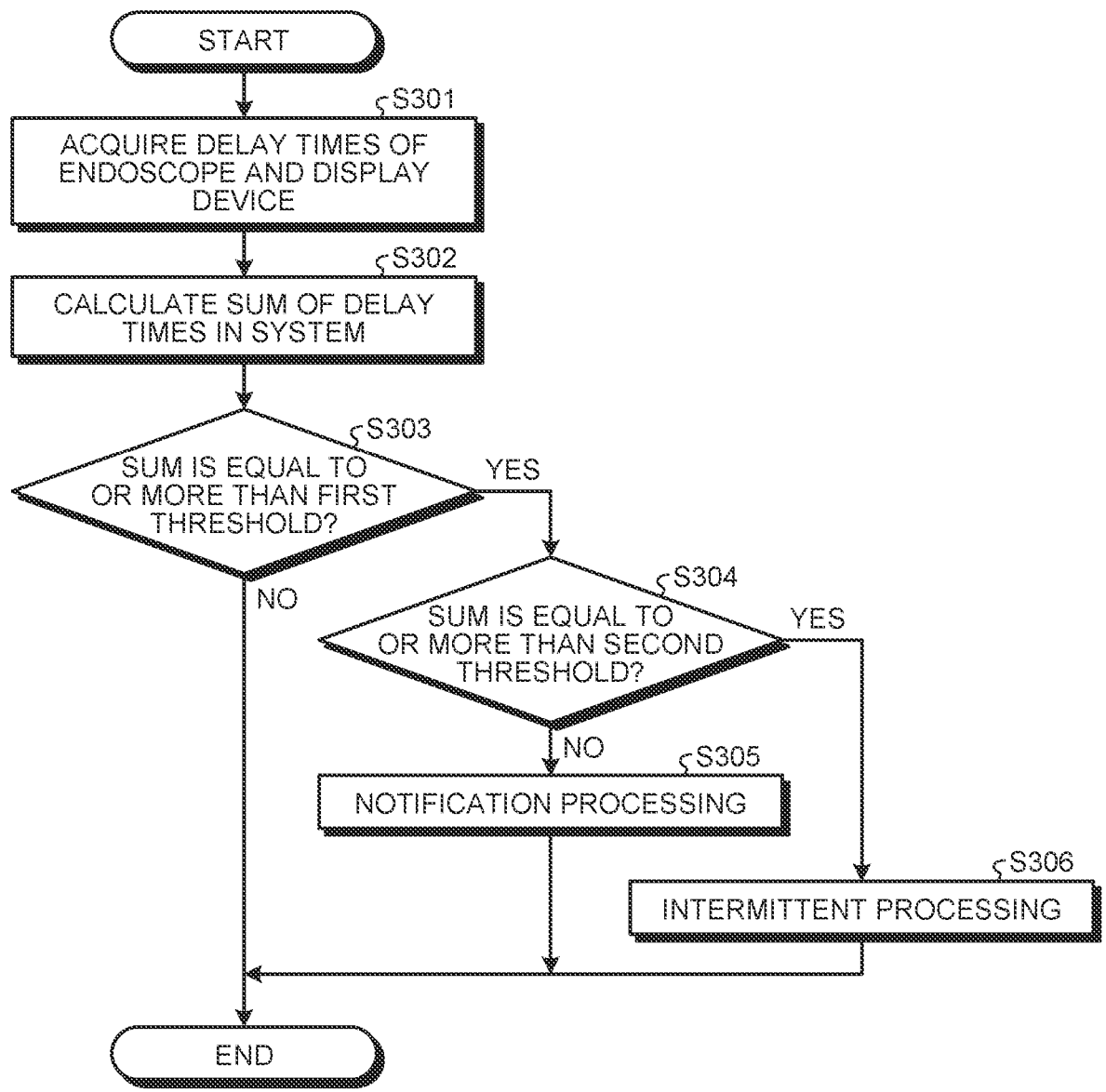
FIG. 7 is a flowchart illustrating delay detection processing performed by an endoscope system according to a third embodiment of the disclosure.

Next, a third embodiment of the disclosure will be described with reference to FIG. 7. FIG. 7 is a flowchart illustrating delay detection processing performed by an endoscope system according to the third embodiment of the disclosure. Note that, since a configuration of the endoscope system according to the third embodiment is the same as that of the above-described endoscope system, the description thereof will be omitted. Hereinafter, processing different from those in the first and second embodiments will be described. In the third embodiment, notification processing or image processing change processing is executed on the basis of a delay time.

When an endoscope 2 and a display device 4 are connected after power is supplied, a processing device 3 acquires processing information (delay time) of each device from memories 247 and 44 (step S301).

In step S302 following step S301, a total delay time detection portion 33 refers to a storage portion 38 to acquire the processing time (delay time) in the processing device 3, and calculates the sum of the delay times of the respective devices.

In step S303 following step S302, a control portion 37 compares the sum of the delay times of the respective devices with a first threshold, and determines whether or not a delay to be notified or subjected to a processing change can occur. Here, the first threshold is a numerical value determined by the number of frames, similarly to the first embodiment and the like.

Here, when the control portion 37 determines that the sum of the delay times of the respective devices is equal to or more than the first threshold, that is, a delay to be notified can occur on the basis of the sum (step S303: Yes), the control portion 37 proceeds to step S304. On the other hand, when the control portion 37 determines that the sum of the delay times of the respective devices is less than the first threshold, that is, that no delay to be notified occurs on the basis of the sum (step S303: No), the control portion 37 ends the delay detection processing.

In step S304, the control portion 37 compares the sum of the delay times of the respective devices with a second threshold, and determines whether or not a delay to be notified can occur. Here, the second threshold is a numerical value determined by the number of frames and is a numerical value larger than the first threshold.

Here, when the control portion 37 determines that the sum of the delay times of the respective devices is equal to or more than the second threshold, that is, a delay to be notified can occur on the basis of the sum (step S304: Yes), the control portion 37 proceeds to step S305. On the other hand, when the control portion 37 determines that the sum of the delay times of the respective devices is less than the second threshold, that is, no delay to be notified occurs on the basis of the sum (step S304: No), the control portion 37 proceeds to step S306.

In step S305, the control portion 37 causes a notification portion 43 of the display device 4 to notify that a delay occurs in the displayed image, similarly to step S104 of the first embodiment. At this time, the control portion 37 causes an image processing portion 31 to perform normal processing of causing each portion (see FIG. 3) of the above-described image processing portion 31 to execute processing.

In step S306, the control portion 37 causes the image processing portion 31 to perform intermittent processing, similarly to step S204 of the second embodiment.

In the third embodiment described above, the delay time generated by the image generation processing in each of the endoscope 2, the processing device 3, and the display device 4 is detected, and whether the notification portion 43 performs notification or contents of the image processing are changed is selected according to the detection result. According to the third embodiment, it is possible to suppress a deviation between an actual position of the endoscope 2 and a position of the endoscope 2 recognized by an operator observing a display image by the notification of the delay or the elimination of the delay.

Fourth Embodiment

Figure 8:
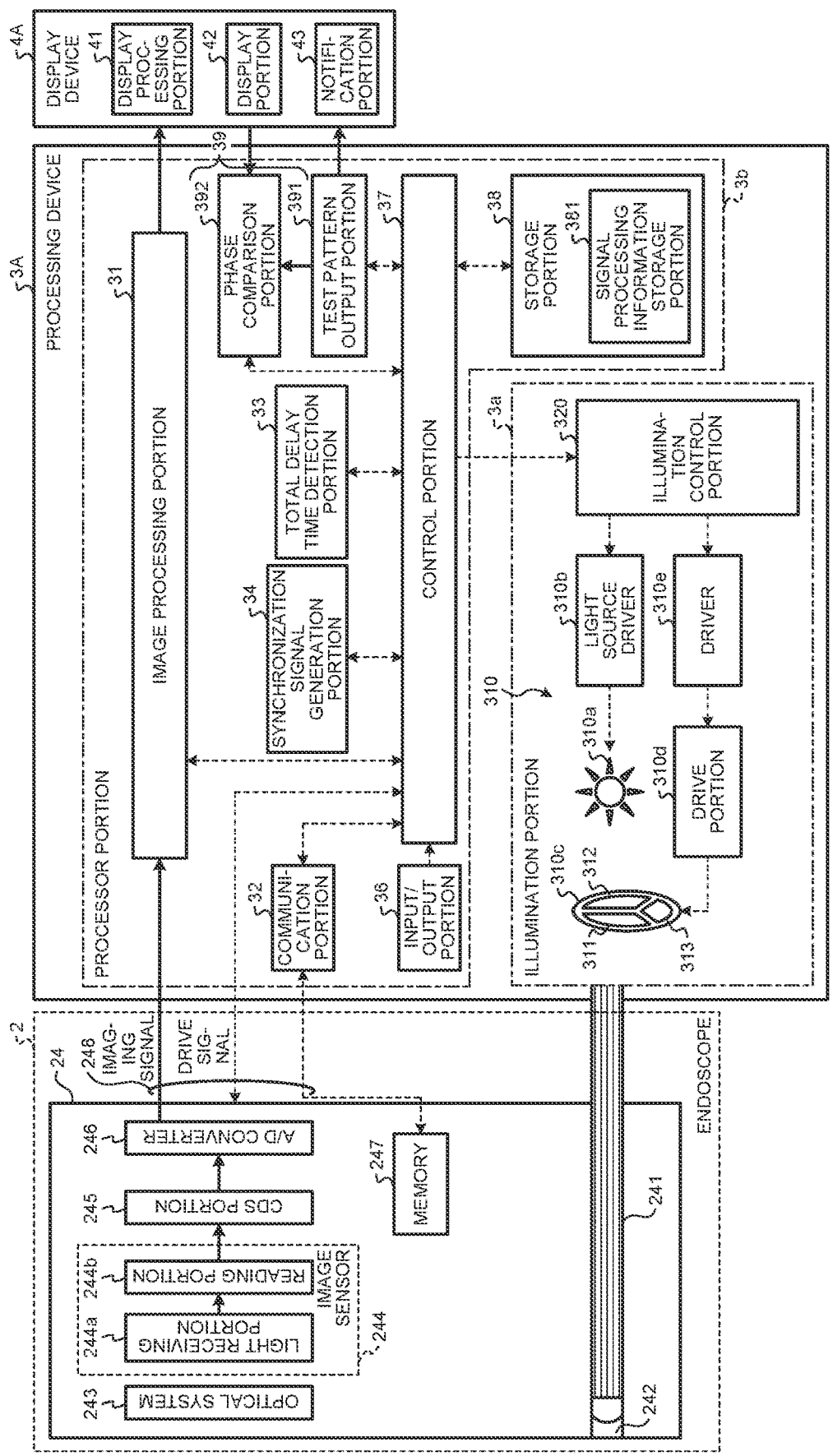
FIG. 8 is a block diagram illustrating a schematic configuration of an endoscope system according to a fourth embodiment of the disclosure.

Next, a fourth embodiment of the disclosure will be described with reference to FIGS. 8 and 9. FIG. 8 is a block diagram illustrating a schematic configuration of an endoscope system according to the fourth embodiment of the disclosure.

An endoscope system 1A illustrated in FIG. 8 includes an endoscope 2 that captures an image of a subject by inserting a distal end portion into the subject, a processing device 3A that has an illumination portion 3a generating illumination light emitted from the distal end of the endoscope 2, performs predetermined signal processing on an imaging signal captured by the endoscope 2, and generally controls the entire operation of the endoscope system 1A, and a display device 4A that displays an in-vivo image generated by the signal processing of the processing device 3A. The endoscope system 1A according to the fourth embodiment has the same configuration except that a processing device 3 of an endoscope system 1 described above is changed to the processing device 3A and a display device 4 is changed to the display device 4A. Hereinafter, a configuration different from that of the first embodiment will be described.

The display device 4A displays a display image corresponding to image data received from the processing device 3A (image processing portion 31) via a video cable. The display device 4A includes a display processing portion 41, a display portion 42, and a notification portion 43. The display device 4A according to the fourth embodiment has a configuration not including a memory 44 described above. Therefore, the processing device 3A cannot acquire a delay time from the display device 4A. A configuration including the memory 44 may be adopted, but in the fourth embodiment, the delay time is not stored.

The processing device 3A includes an illumination portion 3a, an image processing portion 31, a first communication portion 32, a total delay time detection portion 33, a synchronization signal generation portion 34, an input/output portion 36, a control portion 37, a storage portion 38, and a delay time acquisition portion 39. The processing device 3A is configured to include the delay time acquisition portion 39 instead of the second communication portion 35 in the processing device 3 described above. Hereinafter, the delay time acquisition portion 39 will be described.

The delay time acquisition portion 39 includes a test pattern output portion 391 and a phase comparison portion 392. The delay time acquisition portion 39 is configured using a general-purpose processor such as a CPU or a dedicated processor such as various arithmetic circuits executing specific functions such as an ASIC.

The test pattern output portion 391 outputs image data of a predetermined pattern to the display device 4A.

The phase comparison portion 392 compares phases of the image of the pattern output by the test pattern output portion 391 and the pattern of the display image processed in the display device 4A. Here, the phase refers to an appearance pattern of brightness of sequentially output images. The phase comparison portion 392 obtains a phase difference between the image of the pattern output by the test pattern output portion 391 and the pattern of the display image processed in the display device 4A as a delay time.

FIG. 9 is a diagram illustrating delay time acquisition processing performed by the endoscope system according to the fourth embodiment of the disclosure, and is a timing chart illustrating pattern output timing and display timing. In FIG. 9, a horizontal axis represents the lapse of time. (a) of FIG. 9 illustrates an image corresponding to the pattern output from the test pattern output portion 391. (b) of FIG. 9 illustrates the pattern image processed in the display device 4A and input to the phase comparison portion. In the display device 4A, when a test pattern is input from the processing device 3A, processing for display is performed by the display processing portion 41. The image data processed by the display processing portion 41 is input to the phase comparison portion 392. This image data is recognized as an image of the same frame as a frame displayed by the display portion 42.

When the test pattern output portion 391 receives an execution instruction of the delay time acquisition processing of the display device 4A from the control portion 37, the test pattern output portion 391 sequentially outputs test patterns to the display device 4A (see (a) of FIG. 9). Specifically, the test patterns are sequentially output in the order of pattern images $F_{51}, F_{52}, F_{53}, \ldots, F_{59}, F_{60}, \ldots$, and $F_{65}$. In the pattern images $F_{51}, F_{52}, F_{53}, \ldots, F_{59}, F_{60}, \ldots$, and $F_{65}$, test patterns having different brightness are output at preset intervals. In (a) of FIG. 9, the pattern images $F_{55}, F_{60}$, and $F_{65}$ correspond to the test patterns having different brightness.

The test patterns processed in the display device 4A are sequentially input from the display processing portion 41 to the phase comparison portion 392 (see (b) of FIG. 9). Specifically, the test patterns are sequentially output in the order of pattern images $F_{71}, F_{72}, F_{73}, \ldots, F_{79}, F_{80}, \ldots$, and $F_{83}$. Even in the pattern images $F_{71}, F_{72}, F_{73}, \ldots, F_{79}, F_{80}, \ldots$, and $F_{83}$, test patterns having different brightness appear. In (b) of FIG. 9, the pattern images $F_{75}$ and $F_{80}$ correspond to the test patterns having different brightness.

As can be seen from (a) and (b) of FIG. 9, a delay of two frames occurs due to the processing of the display device 4A. The phase comparison portion 392 calculates the delay time by comparing the phases from the brightness between the test pattern output from the test pattern output portion 391 to the display device 4A and the test pattern returned from the display device 4A.

The delay detection processing according to the fourth embodiment is performed according to the processing of the first or second embodiment described above. At this time, the total delay time detection portion 33 acquires the delay time calculated by the phase comparison portion 392 (steps S101 and S201).

In the fourth embodiment described above, even when the delay time of the display device 4A is unknown, the test patterns are output, the phases are compared, and the delay time is acquired. According to the fourth embodiment, even in a device with an unknown delay time, it is possible to acquire the delay time of the device and perform processing according to the delay time.

Note that, in the above-described first to fourth embodiments, it has been described that the illumination portion 3a is configured separately from the endoscope 2, but for example, a configuration in which a light source device is provided in the endoscope 2, such as providing a semiconductor light source at the distal end of the endoscope 2, may be adopted. Further, the functions of the processing devices 3 and 3A may be given to the endoscope 2.

Further, in the above-described first to fourth embodiments, it has been described that the illumination portion 3a is integrated with the processing devices 3 and 3A, but the illumination portion 3a and the processing device 3 may be separated, and for example, the light Source portion 310 and the illumination control portion 320 may be provided outside the processing devices 3 and 3A.

Further, in the above-described first to fourth embodiments, a part of the functions of the processor portion 3b may be executed by the endoscope 2 or the display device 4. For example, the total delay time detection portion 33 may be provided in the endoscope 2 or the display device 4 to detect the delay time in devices other than the processing devices 3 and 3A.

Further, in the above-described first to fourth embodiments, the endoscope system according to the disclosure has been described as the endoscope system 1 using the flexible endoscope 2 in which the observation target is a living tissue or the like in the subject. However, the disclosure can also be applied to an endoscope system using a rigid endoscope, an industrial endoscope for observing characteristics of a material, a capsule endoscope, a fiber scope, or an optical endoscope such as an optical visual tube in which a camera head is connected to an eyepiece.

According to the disclosure, it is possible to suppress a deviation between an actual position of an endoscope and a position of the endoscope recognized by an operator viewing a display image.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
    an endoscope configured to capture an image, generate an imaging signal based on the image captured, and output the imaging signal;
    an image processing device configured to receive the imaging signal, perform image processing on the imaging signal and output the imaging signal subjected to the image processing;
    a display configured to receive the imaging signal subjected to the image processing and display a display image based on the imaging signal subjected to the image processing; and
    a first processor comprising hardware, the first processor being provided in any one of the endoscope, the image processing device, and the display, the first processor being configured to calculate a sum of:
        a first processing time from when the endoscope generates the imaging signal to when the endoscope outputs the imaging signal;
        a second processing time from when the image processing device receives the imaging signal to when the image processing device outputs the imaging signal subjected to the image processing; and
        a third processing time being a processing time for performing processing by the display from when the display receives the imaging signal subjected to the image processing to when the display displays the display image.

2. The endoscope system according to claim 1, wherein:
    the endoscope comprises:
        an image sensor configured to generate the imaging signal by photoelectrically converting received light of the image captured and reading a photoelectrically converted electric signal; and
        a second processor comprising hardware, the second processor being configured to perform signal processing on the imaging signal generated by the image sensor;
    the image processing device comprises a third processor comprising hardware, the third processor being configured to perform a plurality of types of processing on the imaging signal subjected to the signal processing by the second processor received from the endoscope;
    the display comprises a fourth processor comprising hardware, the fourth processor being configured to perform processing for image display on the imaging signal subjected to the plurality of types of processing by the third processor received from the image processing device; and
    the first processing time includes time required for generating the image signal by the image sensor and the signal processing performed by second processor, the second processing time includes time required for performing the plurality of types of processing by the third processor, and the third processing time includes time required for performing the processing for image display by the fourth processor.

3. The endoscope system according to claim 1,
wherein the first processor is configured to:
    determine whether the sum of the first to third processing time is equal to or more than a predetermined threshold; and
    in response to determining that the sum of the first to third processing time is equal to or more than the predetermined threshold, control a notification portion to notify that a deviation occurs between a current position of the endoscope and a position of the endoscope recognized from the image displayed on the display.

4. The endoscope system according to claim 1, wherein:
    the image processing device comprises a third processor comprising hardware, the third processor being configured to perform a plurality of types of processing on the imaging signal sent from the endoscope;
    the first processor is configured to determine whether the sum calculated is equal to or more than a predetermined threshold; and
    the image processing device further comprises a controller configured to, in response to the first processor determining that the sum calculated is equal to or more than the predetermined threshold, cause the third processor to perform intermittent processing in which a part of the plurality of types of processing to be performed by the third processor is thinned out.

5. The endoscope system according to claim 2,
wherein the image processing device further comprises a fifth processor comprising hardware, the fifth processor being configured to:
    output first reference image data that is preset, to the display;
    acquire second reference image data that is obtained by performing the processing on the first reference image data by the fourth processor of the display; and
    compare a phase of the output first reference image data with a phase of the second reference image data to acquire the third processing time required for processing by the fourth processor.

6. The endoscope system according to claim 1, wherein:
the first processing time is stored in the endoscope, the second processing time is stored in the image processing device, and the third processing time is stored in the display; and
the first processor is configured to:
read the first processing time stored in the endoscope, the second processing time stored in the image processing device, and the third processing time stored in the display; and
calculate the sum of the first processing time stored in the endoscope, the second processing time stored in the image processing device, and the third processing time stored in the display read.

7. A method performed by a first processor comprising hardware, the first processor being provided in any one of an endoscope, an image processing device, and a display, wherein:
the endoscope is configured to capture an image, generate an imaging signal based on the image captured, and output the imaging signal;
the image processing device is configured to receive the imaging signal, perform image processing on the imaging signal and output the imaging signal subjected to the image processing; and
the display is configured to receive the imaging signal subjected to the image processing and display a display image based on the imaging signal subject to the image processing, and
wherein the method comprises calculating a sum of:
a first processing time from when the endoscope generates the imaging signal to when the endoscope outputs the imaging signal;
a second processing time from when the image processing device receives the imaging signal to when the image processing device outputs the imaging signal subjected to the image processing; and
a third processing time being a processing time for performing processing by the display from when the display receives the imaging signal subjected to the image processing to when the display displays the display image.

8. A processing device comprising:
a first processor comprising hardware, the first processor being provided in any one of an endoscope, an image processing device, and a display,
wherein:
the endoscope is configured to capture an image, generate an imaging signal based on the image captured, and output the imaging signal;
the image processing device is configured to receive the imaging signal, perform image processing on the imaging signal and output the imaging signal subjected to the image processing; and
the display is configured to receive the imaging signal subjected to the image processing and display a display image based on the imaging signal subject to the image processing, and
wherein the first processor is configured to calculate a sum of:
a first processing time from when the endoscope generates the imaging signal to when the endoscope outputs the imaging signal;
a second processing time from when the image processing device receives the imaging signal to when the image processing device outputs the imaging signal subjected to the image processing; and
a third processing time being a processing time for performing processing by the display from when the display receives the imaging signal subjected to the image processing to when the display displays the display image.

9. The method according to claim 7, wherein:
the endoscope comprises:
an image sensor configured to generate the imaging signal by photoelectrically converting received light of the image captured and reading a photoelectrically converted electric signal; and
a second processor comprising hardware, the second processor being configured to perform signal processing on the imaging signal generated by the image sensor;
the image processing device comprises a third processor comprising hardware, the third processor being configured to perform a plurality of types of processing on the imaging signal subjected to the signal processing by the second processor received from the endoscope;
the display comprises a fourth processor comprising hardware, the fourth processor being configured to perform processing for image display on the imaging signal subjected to the plurality of types of processing by the third processor received from the image processing device; and
the first processing time includes time required for generating the image signal by the image sensor and the signal processing performed by second processor, the second processing time includes time required for performing the plurality of types of processing by the third processor, and the third processing time includes time required for performing the processing for image display by the fourth processor.

10. The method according to claim 7,
wherein the method comprises:
determining whether the sum of the first to third processing time is equal to or more than a predetermined threshold; and
in response to determining that the sum of the first to third processing time is equal to or more than the predetermined threshold, controlling a notification portion to notify that a deviation occurs between a current position of the endoscope and a position of the endoscope recognized from the image displayed on the display.

11. The method according to claim 7, wherein:
the image processing device further comprises:
a third processor comprising hardware, the third processor being configured to perform a plurality of types of processing on the imaging signal sent from the endoscope; and
a controller; and
the method comprises:
determining whether the sum calculated is equal to or more than a predetermined threshold; and
causing the controller to, in response to determining that the sum calculated is equal to or more than the predetermined threshold, cause the third processor to perform intermittent processing in which a part of the plurality of types of processing to be performed by the third processor is thinned out.

12. The method according to claim 9, wherein:
the image processing device further comprises a fifth processor comprising hardware, the fifth processor being configured to:
- output first reference image data that is preset, to the display;
- acquire second reference image data that is obtained by performing the processing on the first reference image data by the fourth processor of the display; and
- compare a phase of the output first reference image data with a phase of the second reference image data to acquire the third processing time required for processing by the fourth processor; and the method further comprises calculating the sum of the first processing time, the second processing time and the third processing time acquired by the fifth processor.

13. The method according to claim 7, wherein:
the first processing time is stored in the endoscope, the second processing time is stored in the image processing device, and the third processing time is stored in the display; and
the method comprises:
- reading the first processing time stored in the endoscope, the second processing time stored in the image processing device, and the third processing time stored in the display; and
- calculating the sum of the first processing time stored in the endoscope, the second processing time stored in the image processing device, and the third processing time stored in the display read.

14. The processing device according to claim 8, wherein:
the endoscope comprises:
- an image sensor configured to generate the imaging signal by photoelectrically converting received light of the image captured and reading a photoelectrically converted electric signal; and
- a second processor comprising hardware, the second processor being configured to perform signal processing on the imaging signal generated by the image sensor;

the image processing device comprises a third processor comprising hardware, the third processor being configured to perform a plurality of types of processing on the imaging signal subjected to the signal processing by the second processor received from the endoscope;
the display comprises a fourth processor comprising hardware, the fourth processor being configured to perform processing for image display on the imaging signal subjected to the plurality of types of processing by the third processor received from the image processing device; and
the first processing time includes time required for generating the image signal by the image sensor and the signal processing performed by second processor, the second processing time includes time required for performing the plurality of types of processing by the third processor, and the third processing time includes time required for performing the processing for image display by the fourth processor.

15. The processing device according to claim 8, wherein the first processor is configured to:
- determine whether the sum of the first to third processing time is equal to or more than a predetermined threshold; and
- in response to determining that the sum of the first to third processing time is equal to or more than the predetermined threshold, control a notification portion to notify that a deviation occurs between a current position of the endoscope and a position of the endoscope recognized from the image displayed on the display.

16. The processing device according to claim 8, wherein:
the image processing device further comprises:
- a third processor comprising hardware, the third processor being configured to perform a plurality of types of processing on the imaging signal sent from the endoscope;
- a controller; and the first processor is configured to:
- determine whether the sum calculated is equal to or more than a predetermined threshold; and
- cause the controller to, in response to the first processor determining that the sum calculated is equal to or more than the predetermined threshold, cause the third processor to perform intermittent processing in which a part of the plurality of types of processing to be performed by the third processor is thinned out.

17. The processing device according to claim 14, wherein:
the image processing device further comprises a fifth processor comprising hardware, the fifth processor being configured to:
- output first reference image data that is preset, to the display;
- acquire second reference image data that is obtained by performing the processing on the first reference image data by the fourth processor of the display; and
- compare a phase of the output first reference image data with a phase of the second reference image data to acquire the third processing time required for processing by the fourth processor; and the first processor is configured to calculate the sum of the first processing time, the second processing time and the third processing time acquired by the fifth processor.

18. The processing device according to claim 8, wherein:
the first processing time is stored in the endoscope, the second processing time is stored in the image processing device, and the third processing time is stored in the display; and
the first processor is configured to:
- read the first processing time stored in the endoscope, the second processing time stored in the image processing device, and the third processing time stored in the display; and
- calculate the sum of the first processing time stored in the endoscope, the second processing time stored in the image processing device, and the third processing time stored in the display read.

* * * * *